United States Patent [19]

Blank et al.

[11] Patent Number: 5,082,976
[45] Date of Patent: Jan. 21, 1992

[54] PROCESS FOR THE PREPARATION OF BENZALDEHYDES

[75] Inventors: Heinz U. Blank, Odenthal; Helmut Kraus, Cologne, both of Fed. Rep. of Germany

[73] Assignee: Bayer Aktiengesellschaft, Leverkusen, Fed. Rep. of Germany

[21] Appl. No.: 603,110

[22] Filed: Oct. 25, 1990

[30] Foreign Application Priority Data

Dec. 1, 1989 [DE] Fed. Rep. of Germany ....... 3939759

[51] Int. Cl.$^5$ .................... C07C 45/32; C07C 45/36
[52] U.S. Cl. .................... 568/431; 568/27; 568/28; 568/30; 568/32; 568/33; 568/41; 568/423; 568/436; 568/437
[58] Field of Search ............ 568/41, 27, 28, 32, 568/33, 423, 431, 437, 436

[56] References Cited

U.S. PATENT DOCUMENTS

| | | | |
|---|---|---|---|
| 3,641,157 | 2/1972 | Riegel | 568/431 |
| 3,661,942 | 9/1972 | Rheenen et al. | |
| 3,931,225 | 6/1976 | Fryer et al. | 568/431 |
| 3,989,674 | 11/1976 | Sinfelt et al. | 568/431 |

FOREIGN PATENT DOCUMENTS

2031416 3/1980 United Kingdom ............... 568/431

OTHER PUBLICATIONS

Patent Abstracts of Japan unexamined applications, C Field, vol. 9, No. 138, pp. 123.

*Primary Examiner*—Werren B. Lone
*Attorney, Agent, or Firm*—Sprung, Horn, Kramer & Woods

[57] ABSTRACT

Benzaldehydes of the formula

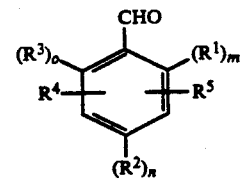

(I)

can be obtained by reaction of substituted β-amino-styrenes of the formula

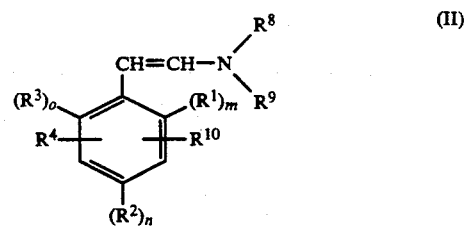

(II)

in which $R^1$, $R^2$, $R^3$, $R^4$, $R^5$, $R^8$, $R^9$, $R^{10}$, m, n and o have the scope of meaning indicated in the description, with oxygen in the presence of a Cu compound in the solution of an aprotic polar solvent at 0°–120° C.

17 Claims, No Drawings

PROCESS FOR THE PREPARATION OF BENZALDEHYDES

BACKGROUND OF THE INVENTION

1. Field of the Invention

The invention relates to a process for the preparation of benzaldehydes which carry an electron-withdrawing substituent in a least one of the ortho- and para-positions.

Such benzaldehydes are important in the preparation of pharmaceutically active preparations, for example, 1,4-dihydropyridine derivatives are prepared from o-nitrobenzaldehyde (DE-OS (German Published Specification) 1,670,827).

2. Description of the Related Art

As the usual classical aldehyde syntheses fail in the synthesis of aldehydes having electron-withdrawing substituents, for example in the synthesis of o-nitrobenzaldehyde, an extensive patent literature about special processes exists to this day. Some of the processes claimed relate in the first step to the side chain halogenation of the underlying o-nitrotoluene with subsequent hydrolysis (DE-OS (German Published Specification) 2,842,360) or oxidation (DE-OS (German Published Specification) 2,708,115), DE-OS (German Published Specification) 2,948,058). However, nuclear halogenation products are always also formed in the side chain halogenation so that complicated purification steps are necessary to obtain o-nitrobenzaldehyde in pharmaceutical quality.

The direct oxidation of o-nitrotoluene using chromium(VI) oxide is problematical because of waste water pollution. With the use of other oxidizing agents, such as cerium(IV) perchlorate (EP 205,173) or cobalt(III) sulphate, the high dilution of the reaction mixture required and the low conversions attainable speak against its realisation as an economical process.

Even in the oxidation of o-nitro-styrene using oxygen in the presence of various catalyst, only low conversions are achieved (DE-OS (German Published Specification) 2,805,402), while the somewhat more complicated use of ozone at $-20°$ C. gives better yields (DE-OS (German Published Specification) 2,829,346). However, the preparation of o-nitro-styrene is troublesome and in turn contains a less desirable halogenation step.

Other processes have therefore been developed for the oxidative degradation of compounds which can be prepared by C-C coupling, starting from inexpensive o-nitrotoluene. The oxidation of 2-nitrophenylpyruvic acid with potassium permanganate (DE-OS (German Published Specification) 2,415,061) or with hypochlorite and subsequent hydrolysis (DE-OS (German Published Specification) 2,415,062) gives yields of only 27 or 36%. The reaction of hydrogen peroxide with 2-nitrophenylpyruvic acid derivatives (EP-92,267) gives 39 to about 50% of o-nitrobenzaldehyde, in each case starting from o-nitrotoluene.

The oxidation of β-dimethylamino-2-nitrostyrene using sodium hypochlorite or using 30% strength hydrogen peroxide has also already been described (JP 60-25,957 (1985)). To this end, 2-nitrotoluene was initially used as a starting material and was reacted with the orthoamide dimethylformamide dimethyl acetal to give β-dimethylamino-2-nitrostyrene. As the described oxidation to the aldehyde is carried out in acetonitrile-water mixtures, dimethylformamide and unreacted o-nitrotoluene must be removed by distillation, which, because of the instability of the nitro-styrenes, is not without risk. The yield when using 30% strength hydrogen peroxide is 55% or 42.5%, relative to the expensive dimethylformamide acetal. When using hypochlorite and then hydrolysing, 68 or 53% of the theoretical yield is obtained. Reworking showed that the yield can be increased to up to 80% of the theoretical yield when using 70% strength hydrogen peroxide; however, the use of highly concentrated hydrogen peroxide is problematical.

In principle, the oxidation of enamines with oxygen is also known (Tetrah. Letters 1968, 3271 and 1968, 3267; U.S. Pat. No. 3,661,942), but the preparation of aldehydes by this method has been described as unselective. The oxidation of heterocyclic enamines with $O_2$ in the presence, for example, of 2-β-amino-vinyl-5-nitro-imidazole to give 5-nitro-imidazole-2-carbaldehyde, has been described as not possible (Ann. 1975, 1465).

SUMMARY OF THE INVENTION

It has now been found that the substituted β-amino-styrenes described further below can be oxidized directly using oxygen to the benzaldehydes which are otherwise only accessible with difficulty and which carry an electron-withdrawing substituent in at least one of the ortho- and para-positions if the reaction is carried out in the presence of a Cu compound.

A process for the preparation of a benzaldehyde which carries an electro-withdrawing substituent in at least one of the ortho- and para-positions, of the formula

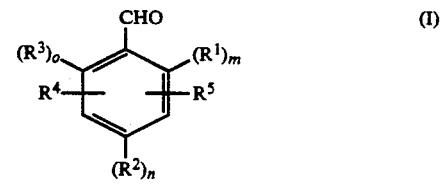

in which $R^1$, $R^2$ and $R^3$ independently of one another denote nitro, cyano, $COOR^6$, $SO_2$—$OR^6$ or $SO_2$—$R^5$, represents hydrogen, straight-chain or branched $C_1$–$C_8$-alkyl, straight-chain or branched $C_1$–$C_8$-alkoxy, phenyl, benzyl, cyclopentyl, cyclohexyl, fluorine, chlorine, bromine or —$N(R^6,R^7)$, denotes hydrogen or the aldehyde group —CHO, where $R^6$ and $R^7$ independently of one another denote straight-chain or branched $C_1$–$C_4$-alkyl, benzyl or phenyl, where, furthermore, the cyclic substituents mentioned may in turn be substituted once or twice by methyl, ethyl, methoxy, ethoxy, fluorine, chlorine or bromine and m, n and o independently of one another can assume the value zero or one, but the sum m+n+o is limited to the value one or two, has been found, which is characterized in that a substituted β-amino-styrene of the formula

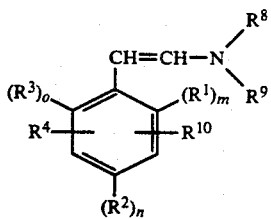

(II)

in which
R[1], R[2], R[3], R[4], m, n and o have the meaning mentioned,

R[8] and R[9] independently of one another denote straight-chain or branched $C_1$–$C_8$-alkyl, $C_5$–$C_7$-cycloalkyl, straight-chain or branched $C_2$–$C_8$-alkenyl, straight-chain or branched $C_2$–$C_8$-alkoxyalkyl, straight-chain or branched $C_3$–$C_8$-alkoxyalkenyl, $C_6$–$C_{12}$-aryl, $C_7$–$C_{10}$-aralkyl or a 5- to 8-membered saturated or unsaturated heterocyclic ring whose heteroatoms are one or two of the group comprising N, O and S, where furthermore
R[8] and R[9], together with the N atom which they substitute, can form a 5- to 8-membered saturated or unsaturated, non-aromatic N-heterocyclic ring which can contain a further heteroatom from the group comprising N, O or S, and
R[8] can additionally denote hydrogen,
R[9] can additionally denote the group

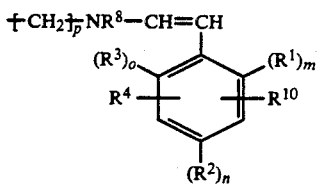

in which
p assumes the value 2, 3 or 4, and
R[10] denotes hydrogen or the group

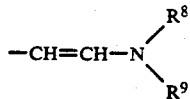

or a mixture of several of such β-amino-styrenes which differ as a result of a different meaning of R[8] and/or R[9],
is reacted with oxygen in the presence of a Cu compound in the solution of an aprotic, polar solvent at 0°–120° C., preferably at 20°–100° C., particularly preferably at 30°–80° C.

DETAILED DESCRIPTION OF THE INVENTION

Straight-chain or branched $C_1$–$C_8$-alkyl is, for example, methyl, ethyl, propyl, isopropyl, butyl, isobutyl, tert.-butyl, or the isomeric pentyl, hexyl or octyl radicals. Preferred alkyl has 1–4 C atoms; methyl and ethyl are particularly preferred.

Straight-chain or branched $C_1$–$C_8$-alkoxy is, for example, methoxy, ethoxy, propoxy, isopropoxy, butoxy, isobutoxy, tert.-butoxy, or the isomeric pentyloxy, hexyloxy and octyloxy radicals. Preferred alkoxy has 1–4 C atoms; methoxy and ethoxy are particularly preferred.

$C_5$–$C_7$-cycloalkyl is, for example, cyclopentyl, cyclohexyl and cycloheptyl, preferably cyclopentyl and cyclohexyl.

Straight-chain or branched $C_2$–$C_8$-alkenyl is, for example, vinyl, propenyl, allyl, butenyl, pentenyl, hexenyl or octenyl and their branched isomers, preferentially alkenyl radicals having 2–4 C atoms.

Straight-chain or branched $C_2$–$C_8$-alkoxyalkyl is, for example, methoxymethyl, methoxyethyl, ethoxymethyl, ethoxyethyl, ethoxypropyl, ethoxybutyl, or ethoxyhexyl, preferably those having 2–4 C atoms.

Straight-chain or branched $C_3$–$C_8$-alkoxyalkenyl is, for example, methoxyvinyl, ethoxyvinyl, methoxypropenyl, methoxybutenyl and the higher homologues, known to the experts, preferably methoxyvinyl and ethoxyvinyl.

$C_6$–$C_{12}$-aryl is, for example, phenyl, naphthyl and biphenyl, preferably phenyl.

$C_7$–$C_{10}$-aralkyl is, for example, benzyl, α- and β-phenyl-ethyl, phenyl-propyl and phenyl-butyl, preferably benzyl.

5- to 8-membered saturated or unsaturated heterocyclic rings which contain one or two heteroatoms from the group comprising N, O and S are known to the expert and can be linked to the N atom which they substitute in their 1-, 2-, 3- or 4-position. Examples of such rings are: pyrrole, furan, thiophene, pyrroline, tetrahydrofuran, tetrahydrothiophene, pyrazole, imidazole, pyrazoline, pyrazolidine, imidazolidine, oxazole, thiazole, oxazoline, oxazolidine, thiazoline, thiazolidine, pyridine, pyran, thiopyran, piperidine, dihydropyran, tetrahydropyran, dihydrothiopyran, tetrahydrothiopyran, pyridazine, pyrimidine, pyrazine, piperazine, oxazine, thiazine, morpholine, thiomorpholine and others.

In the case in which R[8] and R[9], together with the N atom which they substitute, form a 5- to 8-membered ring, this is in any case an N-heterocyclic ring which can be saturated or unsaturated, but is not aromatic. The N-heterocycles suitable from the above enumeration for this purpose can be recognized by the expert; they are always bonded to the styryl group via an N atom. Preferred rings of this type are pyrroline, pyrrolidine, pyrazoline, pyrazolidine, imidazoline, imidazolidine, oxazolidine, thiazolidine, piperidine, piperazine, morpholine and thiomorpholine; among these the completely saturated ring systems are particularly preferred.

Among the substituted β-amino-styrenes of the formula (II) to be reacted are also those which can carry a second substituted β-amino-vinyl group (R[10]) and which therefore give a dialdehyde in the context of the reaction according to the invention. In a preferred manner, the substituent R[10] assumes the meaning hydrogen.

The substituted β-amino-styrenes of the formula (II) to be reacted are in particular characterized by one or two electron-withdrawing substituents which can be in the ortho-, para-, ortho-para or ortho-ortho-position and whose associated aldehydes are accessible with difficulty in pure form in other ways. Of the above-mentioned electron-withdrawing substituents R[1], R[2] and R[3], nitro and cyano are preferred; nitro is particularly preferred.

All cyclic substituents mentioned (benzene nuclei, cycloaliphatic nuclei and heterocyclic nuclei) can in turn be substituted once or twice by methyl, ethyl, methoxy ethoxy, fluorine, chlorine or bromine.

The preparation of the substituted β-amino-styrenes to be employed according to the invention is known and may be described in terms of formulae as exemplified by o-nitrotoluene as starting compound with the aid of bis-(dimethylamino)-ethoxymethane as follows:

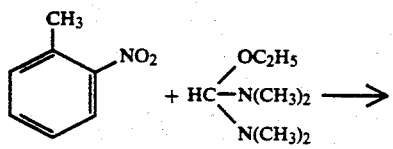

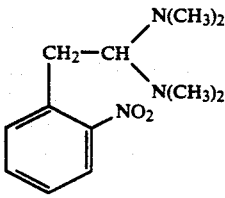

+ C$_2$H$_5$OH

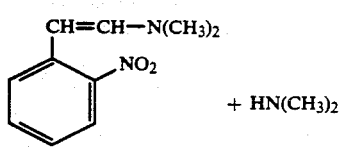

+ HN(CH$_3$)$_2$

It is further known that the above preparation of substituted β-amino-styrenes represented in terms of formulae can also be carried out in the presence of a secondary amine, it being possible for an amine exchange to take place. Thus, in the above formula example in the presence of pyrrolidine, the following mixture can be formed, the cleavage products not being included in the formula equation:

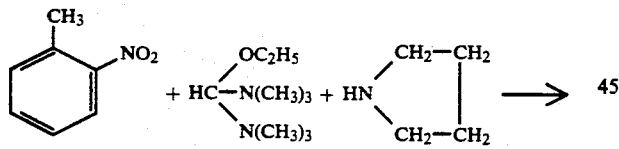

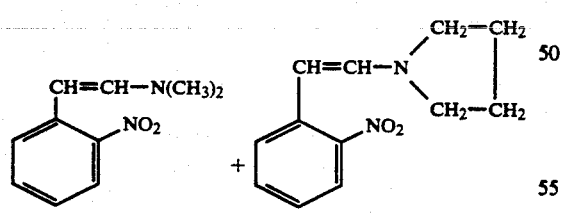

The Cu-catalyzed oxidation, according to the invention, of the substituted β-amino-styrenes can then be represented, for example, as follows:

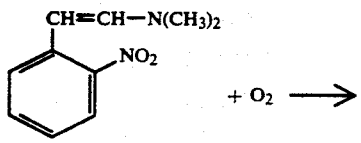

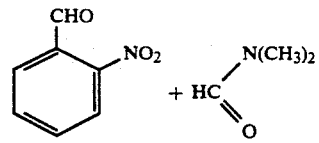

In a preferred manner, substituted β-amino-styrenes of the formula

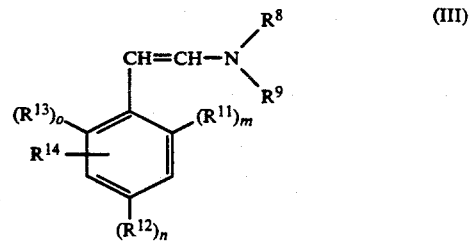

are reacted, in which
R$^8$, R$^9$, m, n and o have the abovementioned meaning,
R$^{11}$, R$^{12}$ and R$^{13}$ independently of one another represent nitro or cyano and
R$^{14}$ denotes hydrogen, straight-chain or branched C$_1$-C$_4$-alkoxy, fluorine, chlorine or bromine.

In a particularly preferred manner, substituted β-amino-styrenes of the formula

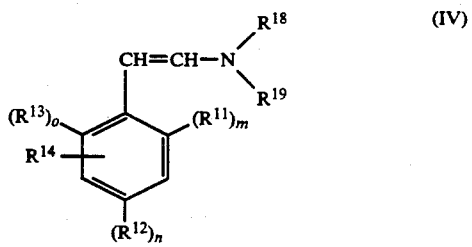

are reacted in the process according to the invention, in which
R$^{11}$, R$^{12}$, R$^{13}$, R$^{14}$, m, n and o have the abovementioned meaning and
R$^{18}$ and R$^{19}$ independently of one another denote straight-chain or branched C$_1$-C$_8$-alkyl, phenyl, benzyl, cyclohexyl or a 5- to 6-membered saturated heterocyclic ring which contains an N or O as heteroatom,
where furthermore
R$^{18}$ and R$^{19}$, together with the N atom which they substitute, form a 5- to 6-membered N-heterocyclic ring which can contain a further heteroatom from the group comprising N and O.

In a very particularly preferred manner, substituted β-amino-styrenes of the formula

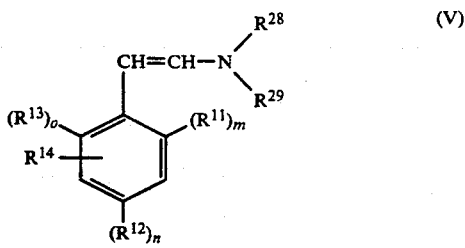

are reacted in the process according to the invention, in which
- $R^{11}$, $R^{12}$, $R^{13}$, $R^{14}$, m, n and o have the abovementioned meaning and
- $R^{28}$ and $R^{29}$ independently of one another denote straight-chain or branched $C_1$–$C_4$-alkyl, benzyl or cyclohexyl, where furthermore
- $R^{28}$ and $R^{29}$, together with the N atom which they substitute, can form the pyrrolidine ring, the oxazolidine ring, the piperidine ring, the piperazine ring or the morpholine ring.

In a furthermore very particularly preferred manner, substituted β-amino-2-nitrostyrenes of the formula

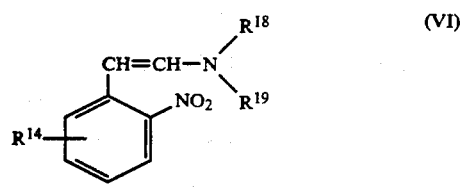

are reacted in the process according to the invention, in which $R^{14}$, $R^{18}$ and $R^{19}$ have the abovementioned scope.

The reaction of compounds of the formula (VI), in which $R^4$ represents hydrogen, to give o-nitrobenzaldehyde is particularly important.

The reaction medium employed is an aprotic polar solvent or a mixture of several of these. Such aprotic polar solvents are preferably substituted acid amides, ketones, sulphoxides and nitriles. Examples of these are dimethylformamide (DMF), dimethylacetamide, diethylformamide, diethylacetamide, hexamethylphosphoramide, acetone, methyl ethyl ketone, methyl tert.-butyl ketone, dimethyl sulphoxide, acetonitrile, propionitrile, N-methyl-pyrrolidone (NMP), N-methyl-caprolactam (NMC) and N,N-dimethyl-imidazolidinone (DMI). In a particularly preferred manner, the substituted acid amides, among them preferably DMF, are employed. The aprotic polar solvent can be partially replaced by an inert solvent. Such inert solvents are, for example, benzene, toluene, xylene, petroleum ether, nitrotoluenes, dimethoxyethane and methyl tert.-butyl ether.

The replacement can be carried out in an amount of 0–50% by weight, relative to the total amount of solvent.

In a preferred variant of the process according to the invention, the substituted β-amino-styrene is employed in the form of the crude product from the preceding aminomethylenation of the underlying substituted toluene, as has been shown above in terms of formulae. As is recognizable from this representation in terms of formulae, substituted formamides of the DMF type are formed in this case as cleavage products which are used in this form as the aprotic polar solvents to be employed according to the invention.

The cleavage products primary alkanol and secondary amine are in general removed from the reaction mixture of the preceding aminomethylenation by distillation, but the process according to the invention is not so sensitive to small amounts of alcohols and amines that such a distillative removal has to be completed with a high outlay.

The process according to the invention is carried out in the presence of a copper compound, in a preferred manner in the presence of an anhydrous copper salt, particularly preferably in the presence of a Cu(I) salt, very particularly preferably in the presence of a Cu(I) halide in an amount of 1–200 mol-%, preferably 5–40 mol-%, particularly preferably 10–20 mol-%, relative to the substituted β-amino-styrene. The copper compound probably reacts at the start of the reaction with oxygen and possible the solvent to give a copper complex whose nature is not exactly known.

The process according to the invention is carried out at a temperature of 0°–120° C., preferably 20°–100° C., particularly preferably 30°–80° C. Oxygen which can be employed is pure oxygen, air enriched with oxygen or atmospheric air itself. In order to minimize the waste gases, pure oxygen or air enriched with oxygen is preferably employed.

In the case in which the process according to the invention is to be combined with the preceding aminomethylenation of the underlying toluene, a process is used, for example, in which the underlying toluene having electron-withdrawing substituents in at least one of the ortho- and para-positions, for example o-nitrotoluene, is reacted with an ortho-amide in a 2-4-fold molar excess in one of the aprotic polar solvents mentioned or an inert solvent. Such an ortho-amide may be, for example, a bis-(dimethylamino)alkoxy methane, such as the tert.-butyl of the ethyl derivative, or an acid amide acetal, for example DMF acetal. When using the last-mentioned acid amide acetal, the reaction times can be shortened by the addition of a secondary amine, for example by the addition of the pyrrolidine shown above in terms of formulae. The resulting alcohol and the amine which may be formed are largely removed by distillation. In this way, starting from the underlying substituted toluene, yields of above 95% can be obtained.

For carrying out of the process according to the invention, an isolated substituted β-amino-styrene or the crude product from the preceding aminomethylenation just described is employed. To this end, all reaction components (solvent, Cu compound and substituted β-amino-styrene) are initially introduced or only the solvent and the Cu compound are initially introduced and the β-amino-styrene is added dropwise in solution. The reaction mixture is fed through a frit or another distribution device using oxygen or an oxygen-containing gas, the temperature being kept in the abovementioned range.

Both process variants mentioned (the substituted β-amino-styrene is either completely introduced initially or metered in in the course of the reaction) can also be carried out under a pressure of, for example, 1.01–50 bar, the substituted β-amino-styrene being pumped in in the second variant.

The amount of aprotic polar solvent or the solvent mixture described above is proportioned using an inert solvent such that during the reaction 100–10,000 ml, preferably 100–1000 ml, particularly preferably 10–500 ml of solvent are present per 10 g of the substituted β-amino-styrene. In the case in which the substituted β-amino-styrene is metered in in the second reaction variant described, for example at the rate of its reaction, it is therefore possible to manage with less solvent than in the first variant where the substituted β-amino-styrene is introduced completely at the start of the reaction. In a particular type of the 2nd variant, the Cu(I) halide is initially only partially added and the rest of the amount intended is metered in in the course of the reaction.

At the end of the reaction, which is evident by the disappearance of the red colour of the substituted β-amino-styrene, the solvent (mixture) is, for example, removed by distillation in vacuo and the residue is added to 3–8N aqueous hydrochloric acid. The benzaldehyde (I) precipitates as a slightly coloured solid and in general already has a purity of more than 95% after drying. 1–5% of benzaldehyde (I) can be present in the filtrate and can be extracted using a suitable solvent, such as methylene chloride.

The yield is up to 90%, relative to the substituted β-amino-styrene and up to 88%, relative to the underlying toluene, for example 80–91% of o-nitrobenzaldehyde, relative to the substituted β-amino-2-nitro-styrene and 85–89%, relative to the underlying o-nitro-toluene. It is possible to dilute the reaction mixture before working-up, for example with pentane, and thus to precipitate one part of the catalytically active copper compound, which can be used again.

The high yield described at the same time together with high purity in the process according to the invention is surprising as a further oxidation of the benzaldehyde (I) formed to the respective benzoic acid had to be taken into account.

EXAMPLES

Example 1

20.6 g of o-nitrotoluene of 24 g of bis-(dimethylamino) ethoxy methane in 50 ml of DMF were initially introduced into a distillation apparatus and the mixture was heated at 120° C. for 6 h to form the β-amino-2-nitrostyrene. The ethanol was then removed by briefly applying vacuum.

2 g of CuCl in 150 ml of DMF were initially introduced into a second flask and aerated at 65° C. with oxygen. After 15 min, the crude solution of the β-amino-2-nitrostyrene was added dropwise in the course of 3 h. 30 min. after completion of the addition, it was no longer possible to detect starting material by thin-layer chromatography, and the mixture was concentrated on a rotary evaporator. it was then introduced into 100 ml of 5N HCl, o-nitrobenzaldehyde being precipitated as a beige-coloured substance. A further product was isolated from the filtrate by extraction with methylene chloride.

Altogether, the yield was 86.6%, starting from o-nitrotoluene. The o-nitrobenzaldehyde precipitated had a purity of 96.2% after drying. The extracted material was purified via the bisulfite adduct.

Example 2

Corresponding to Example 1, 0.15 mol of pyrrolidine was added in the aminomethylenation. A mixture of 86.7% of β-pyrrolidino- and 13.3% of β-dimethylamino-2-nitrostyrene in DMF was obtained, which was oxidized analogously to Example 1.

The yield was 85.1%, starting from o-nitro-toluene.

Example 3

The crude solution of β-dimethylamino-2-nitro-styrene, prepared analogously to Example 1, was diluted with 250 ml of DMF and 3 g of CuCl were added. The mixture was areated at 50° C. for 45 min. using oxygen and the solvent was then removed. After customary working-up, it was possible to isolate 88.8% of o-nitrobenzaldehyde, based on the o-nitro-toluene employed. The proportion of secondary components in the precipitated product was only 0.8%.

Example 4

50 mmol of β-morpholino-2-nitrostyrene and 1 g of CuCl were initially introduced into 120 ml of DMSO and aerated at 60° C. for 90 min. using oxygen. After concentrating and customary working-up, 0.41 mol of o-nitrobenzaldehyde was isolated.

Example 5

20 g of β-dimethylamino-2-nitrostyrene, 1 g of CuCl and 300 ml of DMF were initially introduced into a 300 ml autoclave equipped with an aerating stirrer. The autoclave was heated to 50° C. and pressurized to 10 bar with air, and a pressure of 20 bar was then maintained using oxygen. After 2 h, the experiment was discontinued and 87.2% of o-nitrobenzaldehyde was obtained after working-up.

Example 6

Analogously to Example 1, 0.1 mol of N,N'-dimethyl-ethylenediamine was added during the aminomethylenation. The styrene mixture obtained was diluted using 250 ml of DMF and aerated for 90 min. at 75° C. using oxygen after adding 4 g of CuCl. According to gas chromatographic analysis using an internal standard, 66.3% of o-nitrobenzaldehyde was formed.

Example 7

2.6 g of β-benzylamino-2-nitrostyrene were dissolved in 20 ml of DMF and aerated at 50° C. with oxygen after adding 0.3 g of CuBr. After 2 h, it was possible to detect by thin layer chromatography that the starting material had reacted and o-nitrobenzaldehyde was present.

Example 8

8.6 g of β-dimethylamino-2-cyanostyrene were dissolved in 100 ml of DMF. 0.25 g of CuCl was added and the mixture was aerated for 4 h at 35°–40° C. using oxygen. After the customary aqueous work-up, o-cyanobenzaldehyde was obtained as the product.

What is claimed is:

1. Process for the preparation of a benzaldehyde which carried an electron-withdrawing substituent in at least one of the ortho- and para-positions, of the formula

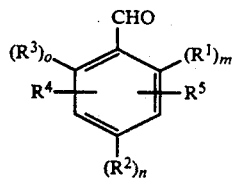

in which
R$^1$, R$^2$ and R$^3$ independently of one another denote nitro, cyano, COOR$^6$, SO$_2$—OR$^5$ or SO$_2$—R$^5$,
represents hydrogen, straight-chain or branched C$_1$-C$_8$-alkyl, straight-chain or branched C$_1$-C$_8$-alkoxy, phenyl, benzyl, cyclopentyl, cyclohexyl, fluorine, chlorine, bromine or —N(R$^6$,R$^7$),
denotes hydrogen or the aldehyde group —CHO, where
R$^6$ and R$^7$ independently of one another denote straight-chain or branched C$_1$-C$_4$-alkyl, benzyl or phenyl,
where, furthermore, the cyclic substituents mentioned may in turn be substituted once or twice by methyl, ethyl, methoxy, ethoxy, fluorine, chlorine or bromine and m, n and o independently of one another can assume the value zero or one, but the sum m+n+o is limited to the value one or two,
wherein a substituted β-amino-styrene of the formula

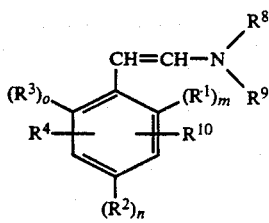

in which
R$^1$, R$^2$, R$^3$, R$^4$, m, n and o have the meaning mentioned,
R$^8$ and R$^9$ independently of one another denote straight-chain or branched C$_1$-C$_8$-alkyl, C$_5$-C$_7$-cycloalkyl, straight-chain or branched C$_2$-C$_8$-alkenyl, straight-chain or branched C$_2$-C$_8$-alkoxyalkyl, straight-chain or branched C$_3$-C$_8$-alkoxyalkenyl, C$_6$-C$_{12}$-aryl, C$_7$-C$_{10}$-aralkyl or a 5- to 8-membered saturated or unsaturated heterocyclic ring whose heteroatoms are one or two of the group comprising N, O and S,
where furthermore
R$^8$ and R$^9$, together with the N atom which they substitute, form a 5- to 8-membered saturated or unsaturated, non-aromatic N-heterocyclic ring which contain a further heteroatom from the group comprising N, O or S, and
R$^8$ additionally denotes hydrogen,
R$^9$ additionally denotes the group

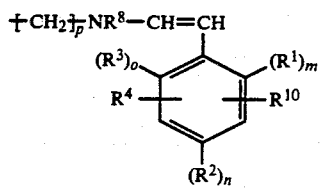

in which
p assumes the value 2, 3 or 4, and
R$^{10}$ denotes hydrogen or the group

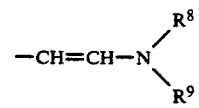

or a mixture of several of such β-amino-styrenes which differ
is reacted with oxygen in the presence of an anhydrous copper salt in the solution of an aprotic, polar solvent selected from the group comprising dimethylformamide (DMF), dimethylacetamide, diethylformamide, diethylacetamide, hexamethylphosphoramide, acetone, methyl ethyl ketone, methyl tert.-butyl ketone, dimethyl sulphoxide, acetonitrile, propionitrile, N-methylpyrrolidone (NMP), N-methyl-caprolactam (NMC) and N,N-dimethyl-imidazolidinone (DMI), at 0°–120° C.

2. The process of claim 1, wherein the reaction with oxygen is carried out at 20°–100° C.

3. The process of claim 2, wherein the reaction with oxygen is carried out at 30°–80° C.

4. The process of claim 1, wherein a substituted β-amino-styrene of the formula

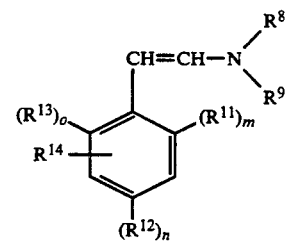

is reacted, in which
R$^8$, R$^9$, m, n and o have the meaning mentioned in claim 1, p1 R$^{11}$, R$^{12}$ and R$^{13}$ independently of one another represent nitro or cyano and
R$^{14}$ denotes hydrogen, straight-chain or branched C$_1$-C$_4$-alkoxy, fluorine, chlorine or bromine.

5. The process of claim 4, wherein a substituted β-amino-styrene of the formula

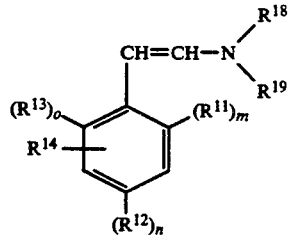

is reacted, in which
R$^{11}$, R$^{12}$, R$^{13}$, R$^{14}$, m, n and o have the meaning mentioned in claim 4 and
R$^{18}$ and R$^{19}$ independently of one another denote straight-chain or branched C$_1$-C$_8$-alkyl, phenyl, benzyl, cyclohexyl or a 5- to 6-membered saturated heterocyclic ring which contains a N or O as heteroatom,
where furthermore
R$^{18}$ and R$^{19}$, together with the N atom which they substitute, form a 5- to 6-membered N-heterocyclic ring which contains a further heteroatom from the group comprising N and O.

6. The process of claim 5, wherein a substituted β-amino-styrene of the formula

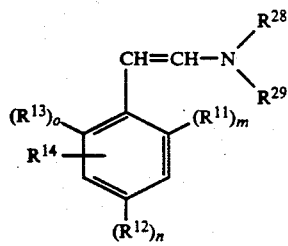

is reacted, in which
$R^{11}$, $R^{12}$, $R^{13}$, $R^{14}$, m, n and o have the meaning mentioned in claim 5 and
$R^{28}$ and $R^{29}$ independently of one another denote straight-chain or branched $C_1$–$C_4$-alkyl, benzyl or cyclohexyl,
where furthermore
$R^{28}$ and $R^{29}$, together with the N atom which they substitute, form the pyrrolidine ring, the oxazolidine ring, the piperidine ring, the piperazine ring or the morpholine ring.

7. The process of claim 6, wherein a substituted β-amino-2-nitro-styrene of the formula

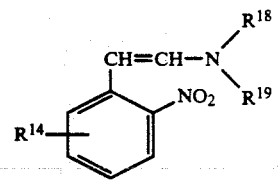

is reacted, in which $R^{14}$, $R^{18}$ have the scope mentioned in claim 5.

8. The process of claim 1, wherein the substituted β-amino-styrene is employed in the form of the crude product form the aminomethylenation of the underlying substituted toluene.

9. The process of claim 1, wherein as the aprotic polar solvent, a substituted acid amide selected from the group comprising dimethylformamide, dimethylacetamide, diethylformamide, diethylacetamide, and hexamethylphosphoramide or a ketone or a sulphoxide is employed, which can be replaced by an inert solvent up to 5–50% by weight, relative to the total amount of solvent.

10. The process of claim 9, wherein a substituted acid amide selected from the group comprising dimethylformamide, dimethylacetamide, diethylformamide, diethylacetamide, and hexamethylphosphoramide is employed as the aprotic polar solvent.

11. The process of claim 10, wherein dimethylformamide is employed as the aprotic polar solvent.

12. The process of claim 9, wherein as the aprotic polar solvent, the solvent from the preceding aminomethylenation is employed in the form of the crude reaction mixture obtained in this case.

13. The process of claim 1, wherein a Cu(I)salt is employed as the Cu compound.

14. The process of claim 13, wherein a Cu(I)halide is employed as the Cu compound.

15. The process of claim 1, wherein the Cu compound is employed in an amount of 1–200 mol-%, relative to the substituted β-amino-styrene.

16. The process of claim 15, wherein the Cu compound is employed in an amount of 5–40 mol-%, relative to the substituted β-amino-styrene.

17. The process of claim 16, wherein the Cu compound is employed in an amount of 10–20 mol-%, relative to the substituted β-amino-styrene.

* * * * *

UNITED STATES PATENT AND TRADEMARK OFFICE
CERTIFICATE OF CORRECTION

PATENT NO. : 5,082,976

DATED : January 21, 1992

INVENTOR(S) : Blank et al.

It is certified that error appears in the above-identified patent and that said Letters Patent is hereby corrected as shown below:

| | |
|---|---|
| Title Page | U.S. PATENT DOCUMENTS: After " 3,661,942 " delete " 9/1972 " and substitute -- 5/1972 --, after " 3,931,225 " delete " 6/1976 " and substitute -- 1/1976 -- |
| Col. 11, line 12 | Delete " $OR^5$ or $SO_2-R^5$ " and substitute -- $OR^6$ or $SO_2-R^6$ -- |
| Col. 11, line 13 | Before " represents " insert -- $R^4$ -- |
| Col. 11, line 17 | Before " denotes " insert -- $R^5$ -- |
| Col. 12, line 41 | Delete " pl " |

Signed and Sealed this

Third Day of August, 1993

Attest:

MICHAEL K. KIRK

Attesting Officer

Acting Commissioner of Patents and Trademarks